(12) United States Patent
Min et al.

(10) Patent No.: US 6,885,892 B1
(45) Date of Patent: Apr. 26, 2005

(54) RATE ADAPTIVE PACEMAKER

(75) Inventors: Mart Min, Tallinn (EE); Andres Kink, Harjumaa (EE); Toomas Parve, Tallinn (EE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/937,971

(22) PCT Filed: Mar. 23, 2000

(86) PCT No.: PCT/SE00/00573

§ 371 (c)(1),
(2), (4) Date: Oct. 1, 2001

(87) PCT Pub. No.: WO00/57954

PCT Pub. Date: Oct. 5, 2000

(30) Foreign Application Priority Data

Mar. 31, 1999 (SE) .............................. 9901195

(51) Int. Cl.$^7$ ............................................. A61N 1/365
(52) U.S. Cl. ..................................................... 607/24
(58) Field of Search ........................... 607/4–9, 17–20, 607/23, 24; 600/483–485

(56) References Cited

U.S. PATENT DOCUMENTS

| | | |
|---|---|---|
| 4,009,721 A | * 3/1977 | Alcidi .......................... 607/22 |
| 5,154,171 A | 10/1992 | Chirife |
| 5,156,147 A | 10/1992 | Warren et al. |
| 5,280,429 A | 1/1994 | Withers |
| 5,282,840 A | 2/1994 | Hudrlik |
| 5,305,745 A | 4/1994 | Zacouto |
| 5,350,409 A | 9/1994 | Stoop et al. |
| 5,383,911 A | * 1/1995 | Mann ........................... 607/19 |
| 5,626,622 A | * 5/1997 | Cooper ......................... 607/18 |
| 5,758,652 A | * 6/1998 | Nikolic ......................... 600/487 |
| 5,792,195 A | 8/1998 | Carlson et al. |
| 5,807,272 A | 9/1998 | Kun et al. |

FOREIGN PATENT DOCUMENTS

| | | | |
|---|---|---|---|
| EP | 0 879 618 | 11/1998 | |
| JP | 64-68279 | * 3/1989 | .................. 607/18 |

* cited by examiner

*Primary Examiner*—Jeffrey R. Jastrzab
(74) *Attorney, Agent, or Firm*—Schiff Hardin LLP

(57) ABSTRACT

A rate adaptive pacemaker has a measuring unit which interacts with a patient to determine a demand, a pacing rate controller connected to the measuring unit for controlling the pacing rate in response to the demand, and a pacing rate limiter connected to the pacing rate controller which upwardly limits the pacing rate so as to always maintain the energy supplied to the myocardium at a level which exceeds the energy consumed by the myocardium.

11 Claims, 3 Drawing Sheets

RATE ADAPTIVE PACEMAKER

BACKGROUND OF THE INVENTION

1. Field of the Invention

The present invention relates to a rate adaptive pacemaker of the type having circuitry for determining the demand of the patient's organism, a pacing rate controller for controlling the pacing rate in response to the patient's demands and a pacing rate limiter for preventing the pacing rate from becoming too high.

2. Description of the Prior Art

Pacing rates that are too high can appear in a rate adaptive pacemaker due to the physical demand of the patient's organism and heart. This may cause lack of oxygen supply to the myocardium. Thus, in certain conditions the heart may not be able to satisfy the physiological needs of the patient's organism and heart if the pacing rate is not limited.

Several different proposals for upwardly limiting the pacing rate have been presented. Thus in e.g. U.S. Pat. No. 5,350,409 a rate adaptive pacemaker is described having an upper pacing limit programmed beyond which rate the pacemaker will not generate and deliver stimulation pulses. U.S. Pat. No. 5,792,195 discloses an acceleration sensed safe upper rate envelope for calculating the hemodynamic upper rate limit for a rate adaptive pacemaker. From the output signal from an accelerometer the time of occurrence of a specific heart sound in relation to a previously occurring ventricular depolarization event is then derived and this heart sound information is used to establish a hemodynamic upper rate limit for the pacemaker. Also European Application 0 879 618 describes a rate modulated heart stimulator having a programmable maximum sensor rate. This heart stimulator also includes an ischemia detector and in response to the detection of an ischemia the maximum allowable stimulation rate is decreased.

The limit values are determined from patients' diagnosis and the setting can be either constant or externally programable.

SUMMARY OF THE INVENTION

An object of the present invention is to provide a rate adaptive pacemaker which continuously automatically upwardly limits the pacing rate according to the current ability of the patient's heart.

The above object is achieved in accordance with the principles of the present invention in a rate adaptive pacemaker having a measurement arrangement for determining a patient's demand, a pacing rate controller which controls the pacing rate in response to the patient's demand, and a pacing rate limiter which prevents the pacing rate from becoming too high. The pacing rate limiter limits the pacing rate upwardly so that a predetermined relation is maintained between the energy supplied to the myocardium and the energy consumed by the myocardium.

Thus, in the pacemaker according to the invention the myocardium energy consumption and energy supply can be kept in balance, and since this relation, and not the heart rate, is of primary importance, the patient can feel more healthy and comfortable in various everyday life conditions, also in conditions of active work. According to the invention the pacing rate limiter is adapted to limit the pacing rate upwardly such that the energy consumed by the myocardium always is less than the energy supplied to the myocardium. In this way lack of oxygen supply to the myocardium is avoided.

According to the invention the pacing rate limiter includes an upper limit setting unit for setting an upper limit value for the pacing rate, and an upper limit determining unit to determine the relation between energy supplied to the myocardium and energy consumed by the myocardium for calculating an upper pacing rate limit value from the relation for supply to the upper limit setting unit. Thus, in this way the actual pacing rate is continuously compared to a set upper limit value and the actual pacing rate is limited to a maximum value equal to this limit value.

In embodiments of the pacemaker according to the invention the pacing rate limiter is adapted to limit the pacing rate such that the inequality $$(t_{diast,\,rest}/t_{diast}) \cdot (SV/SV_{rest}) < CR \tag{1}$$

is satisfied, alternatively the upper limit determining unit is adapted to determine actual coronary resistance ratio (CRR) from the equation $$\text{supplied energy} = \text{consumed energy} \tag{2}$$

and determine an upper pacing rate limit from the relation between actual coronary resistance ratio (CRR) and coronary reserve (CR), or the upper limit determining means is adapted to determine the upper pacing rate limit value from the equation upper pacing rate limit=

$$(60 \cdot CR)/[t_{diast,rest} \cdot (SV/SV_{rest}) + CR \cdot t_{syst}] \tag{3}$$

where $t_{diastrest}$ denotes diastolic duration for the patient in rest conditions, $t_{diast}$ actual diastolic duration for the patient, SV and $SV_{rest}$ actual stroke volume and stroke volume for the patient in rest conditions respectively, and $t_{syst}$ the actual systolic duration. The term "rest condition" is intended to cover not only resting by lying down but also other standard defined low load conditions such as sitting. A bioimpedance measurement unit is preferably provided to measure the intracardiac bioimpedance as a function of time and to determine therefrom the actual stroke volume SV and the actual diastolic and systolic duration $t_{diast}$ and $t_{syst}$ respectively. Since the electrical bioimpedance can be effectively used to determine cardiac parameters, in particular the parameters mentioned above can be obtained from the time variation of the bioimpedance measured between the tip of an intracardiac electrode and the housing of a pacemaker when an excitation current proceeds from the electrode tip, the parameters needed for preventing the pacing rate from becoming too high can be obtained in a very convenient manner by using a standard pacing lead.

where W denotes the work of myocardium, ΔP the mean value of the ventricular pressure variations during a cardiac cycle, and SV the stroke volume.

DESCRIPTION OF THE PREFERRED EMBODIMENTS

As mentioned above, according to one embodiment of the pacemaker according to the invention an upper limit value for the pacing rate is determined based on a balance between the energy consumption of the myocardium and the energy supplied to the myocardium for high patient workloads.

Figure 1A:
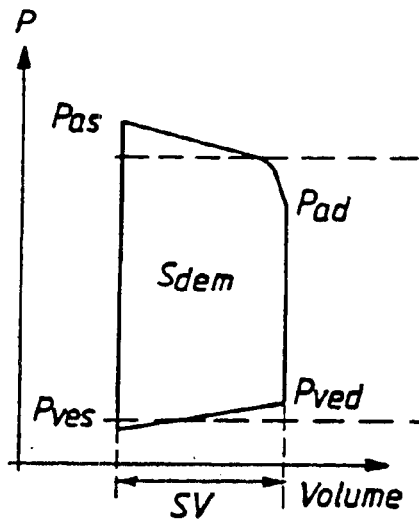
FIG. 1a shows the ventricular pressure-volume loop for a heart rate of 60 beats per minute.

Since the oxygen demand, or demanded energy consumption which is equal to the work of myocardium, is well correlated to the area $S_{dem}$ within the ventricular pressure-volume loop shown in FIG. 1a, the following equations are valid $$W = S_{dem} = \overline{\Delta \bar{P}} \times SV \tag{4}$$

where W denotes the work of the myocardium, $\overline{\Delta \bar{P}}$ the mean value of the ventricular pressure variations during a cardiac cycle, and SV the stroke volume.

Further, in FIGS. 1a, 1b and 2a, 2b, $P_{as}$ denotes the atrial systolic pressure, $P_{ves}$ the ventricular systolic pressure, $P_{ved}$ the ventricular diastolic pressure and $P_{ad}$ the atrial diastolic pressure.

Figure 1B:
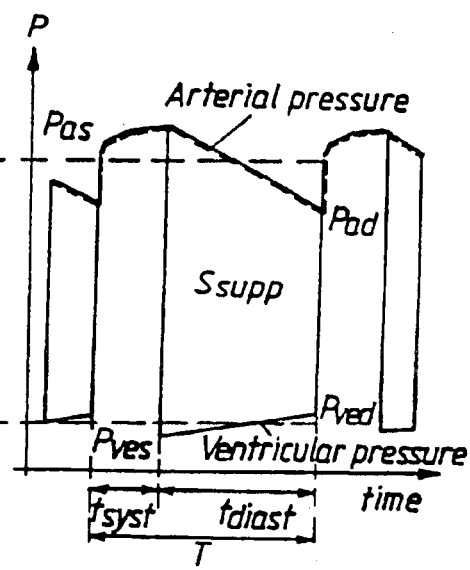
FIG. 1b shows the variation of arterial pressure as a function of time for the same heart rate.
Figure 2A:
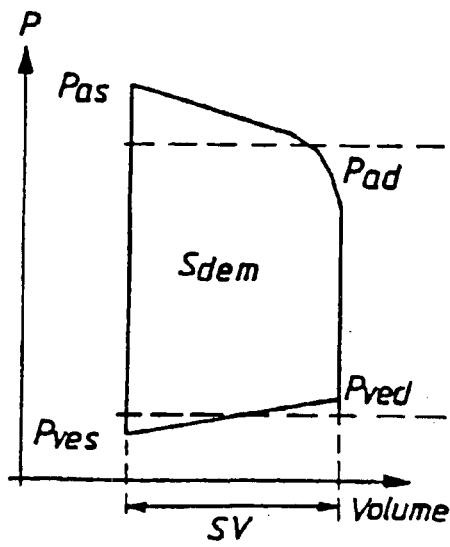
FIGS. 2a and 2b show the corresponding pressure-volume loop and time variation curve for a twice as high heart rate of 120 beats per minute.
Figure 2B:
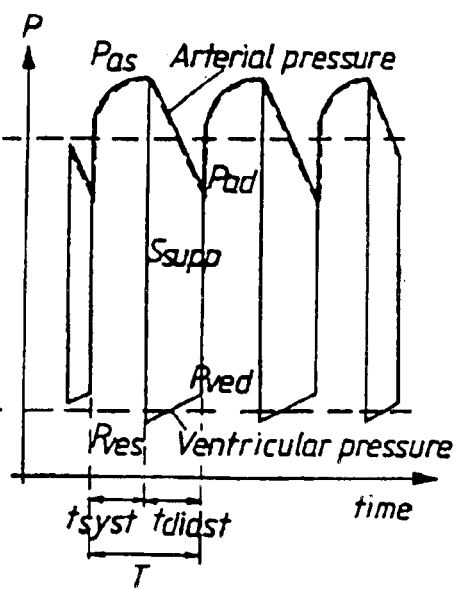

The energy supplied to the myocardium can be derived from the time response curve of the arterial pressure shown in FIG. 1b. The area $S_{supp}$ is namely proportional to the supplied energy E. Thus $$E = S_{supp} \times K = (\overline{\Delta \bar{P}} \times t_{diast}) \times K \tag{5}$$

where $t_{diast}$ denotes the diastolic duration of the patient's heart and K a coefficient essentially representing the conductance for energy influx into the myocardium. The coefficient K can be expressed as $$K = \frac{C_{O_2} \cdot k_{O_2}}{R} \tag{6}$$

where $C_{O_2}$ denotes the difference of the blood oxygen concentration in the artery and vein, i.e. the oxygen uptake, $k_{O_2}$ the energy productivity of blood oxygen, and R the hydraulic resistance of the coronary arteries.

The energy balance W=E results in $$\frac{SV}{t_{diast}} = K \tag{7}$$

Thus, if $$\frac{SV}{t_{diast}} > K \tag{8}$$

the pacing rate must be reduced, because the myocardium does not get sufficient energy, though the patient's organism, i.e. body, can demand even an increase of the pacing rate.

From FIGS. 1a, 1b and 2a, 2b it can be seen that the area $S_{dem}$, representing energy consumed by the myocardium, increases when the heart rate increases, whereas the area $S_{supp}$, which is proportional to the energy supplied to the myocardium decreases with increasing heart rate. Thus it is obvious that for a certain heart rate energy balance can no longer be maintained.

The energy supplied to the myocardium can also be expressed as $$E = V_{mc} \cdot AVD \cdot k_{O_2} \tag{9}$$

where $V_{mc}$ denotes the blood volume flowing through the myocardium during one cardiac cycle and AVD the arterio-venous blood oxygen difference, i.e. equal to the blood oxygen uptake $C_{O_2}$.

The blood volume flowing $V_{mc}$ can be expressed as $$V_{nc} = \int_0^{t_{diast}} f_c(t) \cdot dt = \overline{f_c} \cdot t_{diast} \tag{10}$$

where $f_c(t)$ denotes the blood flow per time unit through the myocardium and $\overline{f_c}$ the mean value of this blood flow.

From equations (9) and (10) the following expression is obtained for the supplied energy E.

$$E = \overline{f_c} \cdot AVD \cdot k_{O_2} \cdot t_{diast} \tag{11}$$

since $$f_c = \frac{\bar{P}}{R} \tag{12}$$

the supplied energy E can be expressed as $$E = \frac{\bar{P}}{R} \cdot (AVD) \cdot k_{O_2} \cdot t_{diast} \tag{13}$$

and consequently the coronary resistance as $$R = \frac{AVD \cdot k_O \cdot t_{diast}}{SV} \tag{14}$$

in the case of energy balance, i.e. E=W.

A well known parameter expressing the work ability of the heart is the coronary reserve CR, which can be expressed as $$CR = \frac{R_{rest}}{R_{min}} \tag{15}$$

where $R_{rest}$ denotes the resistance of the coronary arteries for the patient in rest conditions and $R_{min}$ the minimum value of this resistance. Thus the coronary reserve CR expresses directly the ability of coronary arteries to widen during work, the resistance R then being reduced from $R_{rest}$ to its minimum value $R_{min}$. The coronary reserve varies in a healthy heart from about 4 to 6, but in the case of coronary arteriosclerosis it is lower, typically less than 2.

The current actual value of the ratio $R_{rest}/R$ is called coronary resistance ratio CRR and equals $$CRR = \frac{t_{diast,rest} \cdot AVD_{rest} \cdot k_O \cdot SV}{t_{diast} \cdot AVD \cdot k_{O,rest} \cdot SV_{rest}} \tag{16}$$

Since $k_{O2, rest} = k_{O2}$ and by denoting $$\frac{AVD_{rest}}{AVD} = q \tag{17}$$

q can vary from 1.0 to 0.5, q is decreasing significantly below 1 only in case of anaerobic work of the myocardium.

Arteriovenous difference AVD of the oxygen concentration in blood, i.e. oxygen uptake, does not vary significantly with physical load up to the load allowable for the pacemaker patients, i.e. up to anaerobic load limit. This is so due to autonomous regulation of blood circulation inside the myocardium.

Thus, the coronary resistance ratio CRR can be expressed as $$CRR = \frac{t_{diast,rest}}{t_{diast}} \cdot \frac{SV}{SV_{rest}} \cdot q \quad (18)$$

The coronary resistance ratio CRR expresses the degree of utilization of the coronary reserve CR and when CRR=CR the complete coronary reserve is utilized, which means that the ability of the heart to maintain the energy balance E=W has reached near to its safe limit. If the coronary resistance ratio CRR becomes larger than the coronary reserve CR the pacing rate must be limited.

For q=1 there is no risk for overpacing and for safe limitation of the pacing rate it is suitable to avoid anaerobic operation of the myocardium. Thus the following inequality can be used as criteria for pacing rate limitation.

$$\frac{t_{diast,rest}}{t_{diast}} \cdot \frac{SV}{SV_{rest}} < CR \quad (19)$$

From the equation $$\frac{t_{diast,rest}}{t_{diast}} \cdot \frac{SV}{SV_{rest}} = CR \quad (20)$$

and the relation $$T = t_{diast} + t_{syst} \quad (21)$$

where T denotes the duration of the cardiac cycle in seconds, the following expression is obtained for the upper pacing rate limit in beats per minute upper pacing rate limit=60/T=

$$(60 \cdot CR)/[t_{diast, rest} \cdot (SV/SV_{rest}) + CR \cdot t_{syst}] \quad (22)$$

The parameters stroke volume SV, and the diastolic or systolic durations $t_{diast}$ or $t_{syst}$ are preferably determined from measured time variations of the electric intracardiac bioimpedance, cf. below, and the coronary reserve is obtained by standard physical stress test as using veloergometers or treadmills.

Figure 3:
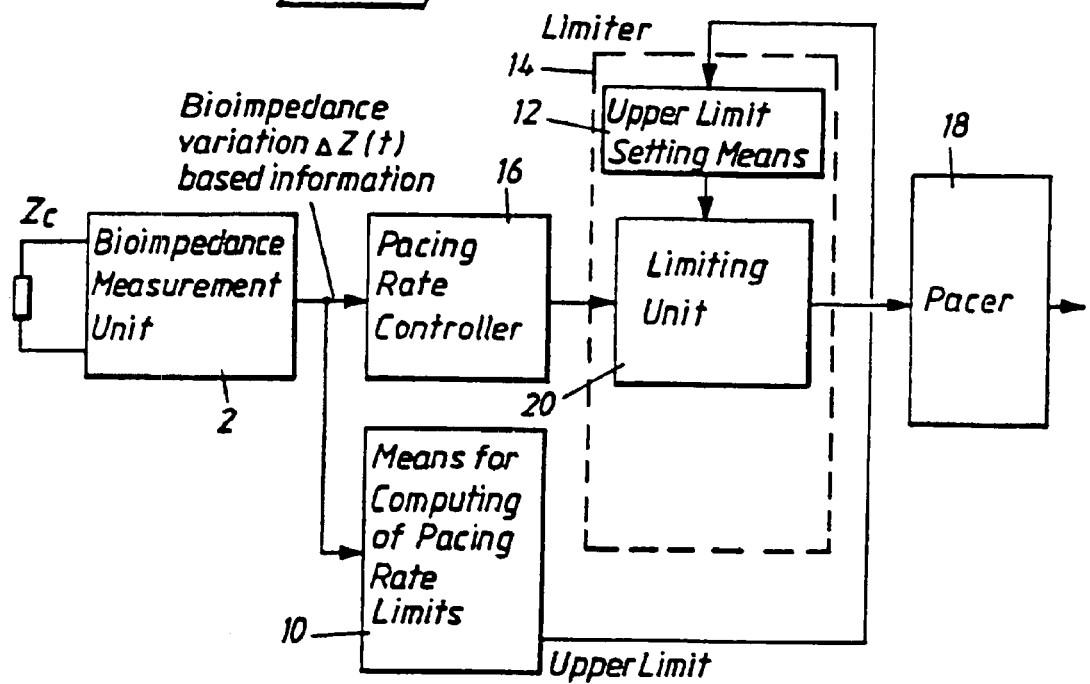
FIG. 3 is a block diagram of an embodiment of the pacemaker according to the invention.
Figure 4:
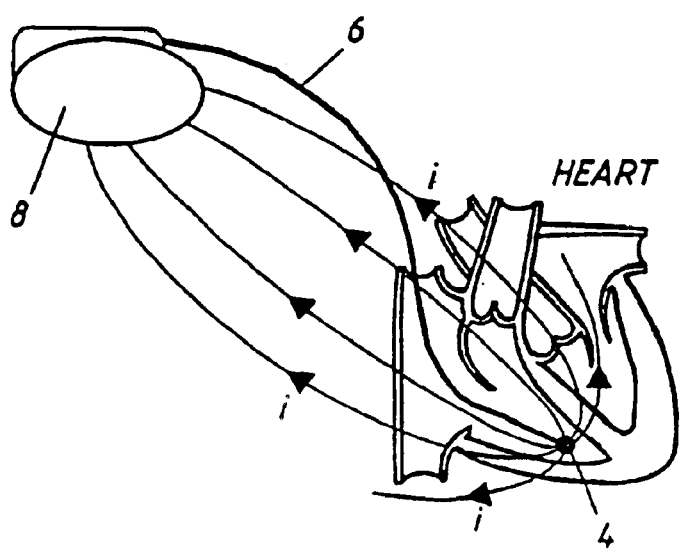
FIG. 4 illustrates the principle of bioimpedance measurement between the tip of an intracardiac electrode and the metal housing of the pacemaker.

FIG. 3 is a block diagram of an embodiment of the pacemaker according to the invention having a bioimpedance measurement unit 2 for measuring the time variation of the electric intracardiac bioimpedance $Z_c(t)$. This type of measurements is well known, see e.g. "Design of Cardiac Pacemakers", edited by John G. Webster, IEEE Press, 1995, pp. 380–386 and U.S. Pat. Nos. 5,154,171, 5,280,429, 5,282,840 and 5,807,272. Thus the time variation of the intracardiac bioimpedance can be measured between the tip 4 of the intracardiac electrode 6 and the housing 8 of the pacemaker, when an excitation current is fed from the electrode tip 4, as schematically illustrated in FIG. 4. Thus a standard pacing lead can be used for this measurement.

From the measured time variations $\Delta Z_c(t)$ the parameters for calculating the upper pacing rate limit according to equation (22) above, or for checking the inequality (19), is determined in a computing unit 10, see FIG. 3.

The calculated upper limit value is supplied to an upper limit setting unit 12 of a pacing rate limiter 14.

A pacing rate controller 16 is also provided for controlling the pacing rate of the pacer or pulse generator 18 in response to the patient's demands. In a limiting unit 20 of the limiter 14 the demanded pacing rate is compared to the set upper limit pacing rate and the actual pacing rate is limited to the set upper limit value if the demanded pacing rate reaches this limit value. Thus in the pacemaker according to the invention an upper limit value for the pacing rate is continuously automatically determined and it is continuously automatically verified that the actual pacing rate does not exceed the present upper limit value. Alternatively, the pacemaker can be modified to continuously monitor that the inequality (19) above is satisfied.

Above bioimpedance measurements are described for determining necessary parameters like stroke volume SV, diastolic or systolic durations $t_{diast}$ or $t_{syst}$. These parameters can, however, also be determined by other techniques. Thus these parameters can be determined from measured ECG's, by ultrasound technique, etc.

Figure 5:
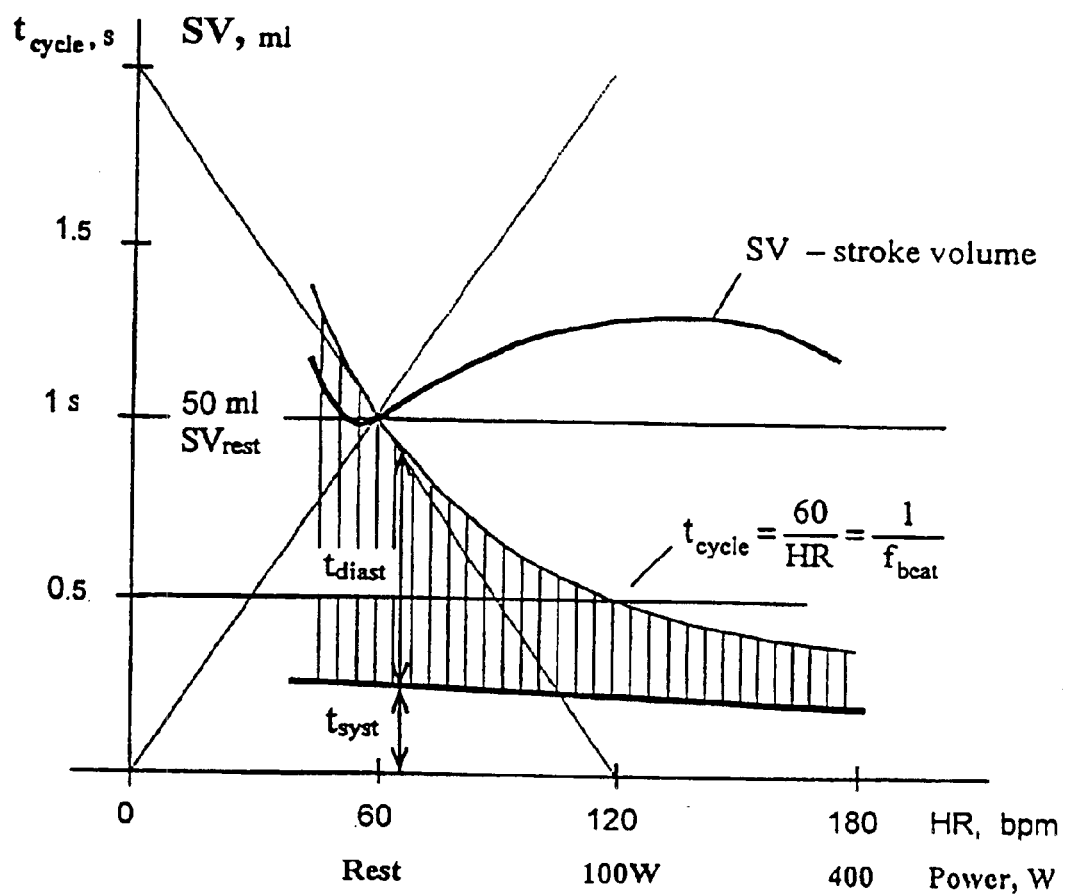
FIG. 5 illustrates the relationships of the cardiac parameters of interest.

The relationships of the cardiac parameters of interest are illustrated in FIG. 5:

If load increases from Rest to some level (e.g. 100 W), the stroke volume SV increases 1.2 to 1.5 times, and the diastole time $t_{diast} = t_{cycle} - t_{syst}$ decreases rapidly with the HR (e.g. 3×).

Falling of the coronary arterial hydraulic resistance due to widening of the blood vessels with the increase of myocardial work $W = S_{dem}$ compensates the decrease of the myocardial energy supply $$E = S_{suppl} \cdot K(C_{O2}; k_{O2}; R).$$

The compensation ability can be expressed by the coronary reserve CR=2 . . . 5 for a typical patient.

Although modifications and changes may be suggested by those skilled in the art, it is the intention of the inventors to embody within the patent warranted hereon all changes and modifications as reasonably and properly come within the scope of their contribution to the art.

We claim:

1. A rate adaptive pacemaker comprising:
   a measuring unit adapted for interaction with a patient for determining a demand;
   a pacing rate controller connected to said measuring unit for controlling a pacing rate in response to said demand; and
   a pacing rate limiter connected to said pacing rate controller, said pacing rate limiter having an upper limit setting unit for setting an upper limit value for said pacing rate, and an upper limit determining unit for determining a relation between energy supplied to the myocardium and energy consumed by the myocardium and for calculating said upper limit value for said pacing rate from said relation for supply to said upper limit setting unit, said pacing rate limiter upwardly limiting said pacing rate to always maintain said energy supplied to the myocardium to exceed said energy consumed by the myocardium.

2. A pacemaker as claimed in claim 1 wherein said pacing rate limiter limits said pacing rate to satisfy $$(t_{diast, rest}/t_{diast}) \cdot (SV/SV_{rest}) < CR$$

wherein $t_{diast,rest}$ denotes a diastolic duration when said patient is at rest, $t_{diast}$ denotes an actual diastolic duration for said patient, SV denotes an actual stroke volume for said patient, $SV_{rest}$ denotes a stroke volume when said patient is at rest, and CR denotes coronary reserve.

3. A pacemaker as claimed in claim 2 wherein said measuring unit is a bioimpedance measuring unit which measures intercardiac bioimpedance as a function of time, and determines SV, $SV_{rest}$, $t_{syst,rest}$ and $t_{diast}$ therefrom.

4. A pacemaker as claimed in claim 2 wherein said measuring unit is an ECG measuring and analyzing unit which obtains an ECG from said patient and which determines SV, $SV_{rest}$, $t_{syst.rest}$ and $t_{diast}$ therefrom.

5. A pacemaker as claimed in claim 1 wherein said upper limit determining unit includes an energy determining unit which determines said energy supplied to the myocardium and said energy consumed by the myocardium, and a comparator which compares said energy supplied to the myocardium and said energy consumed by the myocardium to determine said relation.

6. A pacemaker as claimed in claim 5 wherein said energy determining unit determines said consumed energy as a product of an average value of ventricular pressure variations during a cardiac cycle, and stroke volume.

7. A pacemaker as claimed in claim 5 wherein said energy determining unit determines said supplied energy from a time response curve of arterial pressure during diastole.

8. A pacemaker as claimed in claim 1 wherein said upper limit determining unit determines an actual coronary resistance ratio from an equality between said supplied energy and said consumed energy, and determines said upper pacing rate limit value from a relation between said actual coronary resistance ratio and said coronary reserve.

9. A pacemaker as claimed in claim 1 wherein said upper limit determines said upper pacing rate limit value as equal to $(60 \cdot CR)/[t_{diast,rest} \cdot (SV/SV_{rest}) + CR \cdot t_{syst}]$ wherein CR denotes coronary reserve, $t_{diast.rest}$ denotes a diastolic duration for said patient at rest, SV denotes an actual stroke volume, $SV_{rest}$ denotes a stroke volume for said patient at rest, and $T_{syst}$ denotes an actual scistolic duration.

10. A pacemaker as claimed in claim 9 wherein said measuring unit is a bioimpedance measuring unit which measures intercardiac bioimpedance as a function of time, and determines SV, $SV_{rest}$, $t_{diast.rest}$ and $t_{syst}$ therefrom.

11. A pacemaker as claimed in claim 9 wherein said measuring unit is an ECG measuring and analyzing unit which obtains an ECG from said patient and which determines SV, $SV_{rest}$, $t_{diast.rest}$ and $t_{syst}$ therefrom.

\* \* \* \* \*